United States Patent [19]

Leveson

[11] 4,398,152

[45] Aug. 9, 1983

[54] PHOTOIONIZATION DETECTOR

[76] Inventor: Richard C. Leveson, 288 Newton Dr., Willowdale, Canada M2M2P8

[21] Appl. No.: 353,989

[22] Filed: Mar. 2, 1982

Related U.S. Application Data

[63] Continuation of Ser. No. 177,168, Aug. 12, 1980, abandoned.

[51] Int. Cl.³ .............................................. G01N 27/00
[52] U.S. Cl. ...................................... 324/465; 324/464
[58] Field of Search ................................ 324/464, 465

[56] References Cited

U.S. PATENT DOCUMENTS 2,544,078  3/1951  Glassbrook ......................... 324/464
3,223,873  12/1965  Hampton .............................. 324/464

Primary Examiner—Michael J. Tokar
Attorney, Agent, or Firm—Hirons, Rogers & Scott

[57] ABSTRACT

A gas discharge tube is provided for use in a detector of the type capable of identifying ionizable species in a carrier gas. The tube contains an inert gas at reduced pressure and the gas is excited by an external circuit including a coil about the tube. The circuit generates a radio frequency which excites the gas and emits ultraviolet radiation. This radiation passes through a transversely located window at the end of the tube for ionizing the species in a chamber. Electrodes are also described for use in association with the chamber to sense ionization. These electrodes form part of a sensing circuit.

5 Claims, 8 Drawing Figures

PHOTOIONIZATION DETECTOR

This is a continuation application of application Ser. No. 06/177,168, filed 08/12/80, and now abandoned.

BACKGROUND OF THE INVENTION

1. FIELD OF THE INVENTION

This invention relates to a method and apparatus for the detection of ionized species in a gas carrier, and more particularly to an improved radiation source for producing ionizing radiation in a photoionization detector and to an improved method of irradiating an ionization chamber to create more efficient ionization of at least some of the species.

2. DESCRIPTION OF THE PRIOR ART

Photoionization detectors are available for use with a gas chromatograph column. Ultraviolet radiation is concentrated in an ionization chamber which receives the output from the column. This output consists of a carrier gas and the chemical species being studied. The photon energy of the radiation is at a level designed to selectively ionize the species to be detected rather than the carrier gas. Such ionization is detected by an electrical circuit connected to electrodes in the chamber to provide both a direct read-out and to drive a chart recorder.

In gas chromatography, the carrier gas flows continuously through the device, passing first through the chromatograph column and then through the ionization chamber. A gaseous or liquid diluent, containing the ionizable chemical species under study, is introduced into the stream of carrier gas to be carried through the column to elute at different rates. This causes a time separation of the species so that they can be identified individually (or at least in small groups) in the photoionization detector. When displayed on a chart recorder, the time separation results in the species appearing as a series of peaks whose arrival time is a function of the time taken for that particular species to elute through the column before being ionized. By comparison with known standards, the species can be identified and their quantity measured by using the area under the peak displayed on the chart recorder.

The radiation used in a photoionization detector should be of high enough energy to ionize the chemical species to be detected, but not so high as to discernably ionize the carrier gas or any other species present which it is not desired to detect. Generally speaking the radiation used is ultraviolet radiation in the range 1000 A.U. to 2000 A.U. Such radiation will not ionize any of the permanent air gases, nor will it ionize water vapour. The radiation is quickly absorbed in air so that to be useful it is used in a vacuum or an atmosphere of inert gas. Because of this it is commonly referred to as vacuum ultraviolet radiation.

Presently, the radiation source is commonly a gas discharge tube maintained at low pressure and having a crystal window of an appropriate transmissive material to provide an exit for the ultraviolet radiation. The discharge or excitation is produced by maintaining a constant high potential across two metal electrodes within the tube and in contact with the gas.

In a discharge tube of the above type, complicated tube designs have to be used in order to prevent electrode erosion caused by ion impact. This problem is referred to as "sputtering" and can result in electrode metal being deposited upon the inner surface of the crystal window with resulting reduction in transmission through the window.

U.S. Pat. No. 3,933,432 to Driscoll issued on Jan. 20, 1976 and is an example of a prior art structure which is designed to minimize sputtering. In this structure, the gas discharge has been mainly confined to a central capillary within the discharge tube by constraining the flow of ions as they move from one electrode to another. This design creates what is effectively a "point source" of vacuum UV radiation, originating from the small cross section of the capillary. As a result, the distribution of radiative flux across the diameter of the ion chamber in any plane perpendicular to the direction of travel of the radiation entering the chamber is non-uniform. There is a high concentration at the centre and a low concentration at the periphery. Apart from the reduced ionization due to limited total flux, such a design will exhibit strong "quenching" effects whenever a trace of oxygen is present in the chamber. Such quenching occurs when an electron, generated as a result of photoionization, becomes attached to an oxygen atom, due to the high electron affinity of oxygen. The resulting negative ion has a mobility far lower than the original electron, and is far more likely to recombine with a positively charged ion before it can be detected. Quenching is therefore a severe problem in such a device.

Discharge tubes have also been built with metal electrodes mounted externally of an all-glass tube in a capacitive relationship. For example, U.S. Pat. No. 3,996,272, to Young shows a structure having one electrode inserted into a hollow re-entrant capillary running up the axis of a cylindrical discharge cavity, and a second electrode formed as a metal cylinder wrapped around the outside of the tube. The resulting coaxial electrode configuration functions as a capacitor and is driven by a supply of radio frequency power. Tubes of this type are relatively difficult and expensive to make and, due to obstruction by the re-entrant capillary, do not have a radially uniform output intensity at the window.

In accordance with one aspect of the present invention, a source of photoionization is provided for use in a detector. The source is in the form of an electrodeless gas discharge tube which is excited inductively by the use of a coil connected to a radio frequency oscillating circuit. The inductance coil is provided around the outside of the tube and is tuned to excite radiatively, the gas in the tube so that ultraviolet radiation is emitted through a window in the end of the tube.

In another of its aspects, the invention provides a photoionization detector using the aforesaid source of photoionization in which the window also forms an end wall of an ionization chamber so that the ultraviolet radiation can travel into the ionization chamber. Electrodes are positioned such that the ultraviolet radiation will not impinge on the cathode.

The inductive coil excites the gas in the tube across its whole cross-sectional area and thus produces a uniform distribution across this area which corresponds in size both to the window and to the ionization chamber. As a result the chamber is irradiated substantially uniformly with respect to a plane extending transversely of the axis of the tube and hence of the coil.

These and other aspects of the invention will be better understood with reference to the following description taken in combination with the drawings.

BRIEF DESCRIPTION OF THE DRAWINGS

The invention will be better understood with the following reference to the drawings in which.

DETAILED DESCRIPTION OF THE INVENTION

Figure 1:
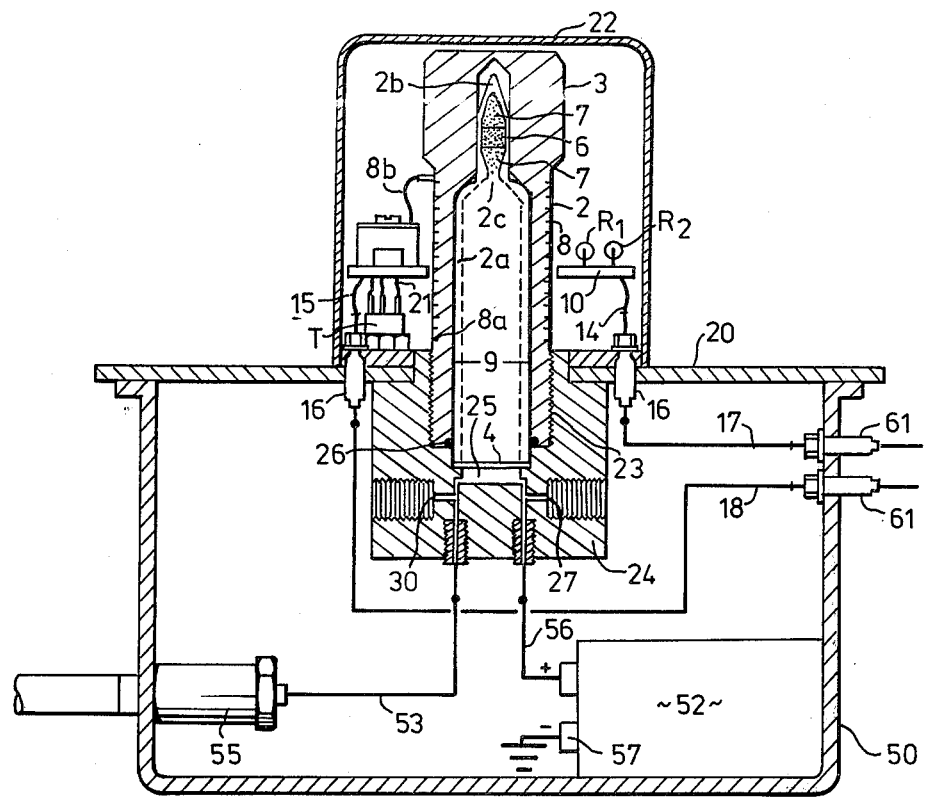
FIG. 1 is a preferred embodiment of a photoionization detector according to the invention and incorporating a preferred form of a gas discharge tube.

As seen in FIG. 1, a glass discharge tube 2 is held in a cylindrical holder 3 of polytetrafluoroethylene (sold under the trade mark Teflon). This material is electrically insulating with low dielectric loss. The discharge tube 2 has a main cylindrical portion 2a of outside diameter ½ inch and inside diameter ⅜ inch and is approximately 1¾ inches in length. At its lower end (as drawn), the cylindrical portion is bonded to a ½ inch diameter by 1 millimeter thick crystal window 4 of magnesium fluoride. The window is preferably bonded to the tube using silver chloride applied at high temperature to platinized surfaces on the glass and crystal. The other end of the cylindrical portion of the discharge tube tapers to a bulb or terminal portion 2b having an outside diameter of ¼ inch and a length of approximately ⅝ inch and is sealed at its end. A constriction 2c is formed between the main and terminal portions of the tube in order to retain, within the terminal portion, a getter compound 6 composed of finely divided barium metal. The barium is secured in place by two plugs of glass wool 7 and the tube is filled with pure krypton gas at a pressure in the range 3.0 to 3.5 Torr.

A coupling inductor 8 is wound around a spiral groove in the outside of the holder 3. One end 8a of the inductor penetrates the holder and makes contact with a metal foil strip 9 coaxially lining the inner wall of the holder 3. The width of the strip is preferably about ⅝ inch and its purpose is to shape the electromagnetic field and aid in the firing of the discharge tube. The foil strip should be positioned relative to the window end of the tube and should not be so wide that it blocks radio frequency radiation emerging from the inductor 8. The other end of the inductor 8b runs to an annular printed circuit board 10 which encircles the holder 3 and carries some parts of the oscillator circuit which includes a radio frequency transistor T, a tuning capacitor C, resistors R1 and R2, and other components not shown in FIG. 1, but illustrated in FIG. 5.

Figure 5:
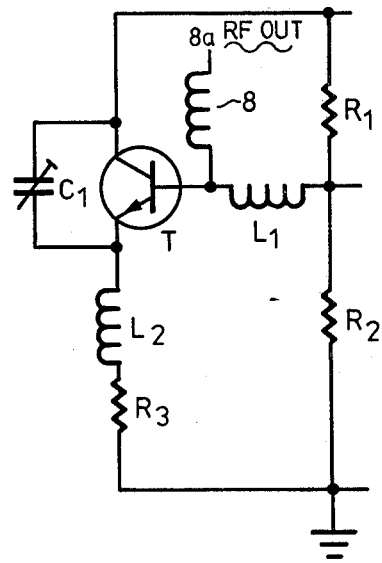
FIG. 5 is a schematic of an oscillator circuit used to energize an inductor which in turn energizes the gas in the discharge tube.

The oscillator circuit, which operates at approximately 100 MHz, is shown in FIG. 5. As seen in FIG. 1, it is connected to a direct current power supply by leads 14 and 15. The following are preferred components:

| | | |
|---|---|---|
| RF Transistor | T | NPN (2N3375) |
| Resistor | $R_1$ | 820 ohm |
| Resistor | $R_2$ | 100 ohm |
| Resistor | $R_3$ | 10 ohm |
| Inductor | $L_1$ | .33 uH |
| Inductor | $L_2$ | .33 uH |
| Capacitor | $C_1$ | 7-25 pf (Trimmer) |

Both power supply leads 14 and 15 pass to the annular circuit board 10 through two radio frequency interference filters 16 (sold under the trade mark FILTERCON by Erie Co.). 28 Volt DC power is supplied to the circuit via leads 17 and 18 and the filters 16 are mounted on a metal bulkhead 20 which supports the photoionization detector.

The transistor T is screwed into the metal bulkhead 20 for heat sinking purposes. Flying leads 21 connect T to the circuit board 10. As also shown in FIG. 1, a deep metal cup 22 is positioned over the gas discharge tube assembly and, together with the metal bulkhead 20, shields the system from both leakage outwards of radio frequency radiation and from leakage inwards of stray electromagnetic radiation. The holder 3 is provided with a male screw thread 23 at its lower end and this portion of the holder penetrates the metal bulkhead 20 and screws into an electrically insulating body 24 of polytetrafluoroethylene (TEFLON trade mark). The body 24 forms a cylindrical ionization chamber 25 which is bounded on one surface by the window 4 of the discharge tube 2. The chamber is 2 mm. long (measured axially) and has a diameter corresponding to that of the internal diameter of the gas discharge tube.

In order to prevent leakage between the ionization chamber 25 and the discharge tube 2, a silicone-rubber O ring is provided as a seal 26. This is held in compression by screwing the holder 3 firmly in place.

In operation, a continuous stream of conventional carrier gas or gases enters the chamber 25 from a conventional gas chromatograph column (not shown) through inlet passages 27 and 28. The sample containing the species to be detected is injected into the carrier gas stream at the inlet to the chromatography column and the species are separated in the column before entering the ionization chamber sequentially. The species are ionized and accelerated by an electrical field between two electrodes 31 and 32 (FIG. 1A) and the positively ionized species are collected by the one of the electrodes which is wired as a cathode. The collected ions produce a response at the electrodes which is passed to an electrometer. When displayed on a chart recorder, each response appears as a peak whose arrival time depends upon the time taken for that particular species to elude through the column and to be ionized. Carrier gas leaves the ionization chamber via passages 29 and 30.

Electrode 31 (FIG. 1A) is preferably the anode and is positioned in the ionization chamber at the inner end of the gas entrance channel 28. Electrode 32 is preferably the cathode and is positioned opposite the electrode 31 at the inner end of exit channel 29. It is preferable to have the cathode in very close proximity to the ionizing region in order to enhance ion collection efficiency while screening the cathode from direct impingement of ultraviolet radiation which would create an undesirable photoelectron current.

The electrodes 31 and 32 are made of platinum wire and in the electrode configuration is best shown in FIG.

2 where it will be seen that the electrodes are located inside an annular recess 33 machined around the cylindrical wall of the ionization chamber 25. The arrangement is such that ultraviolet radiation progressing axially from the discharge tube 2 does not impinge directly upon them.

Figure 1A:
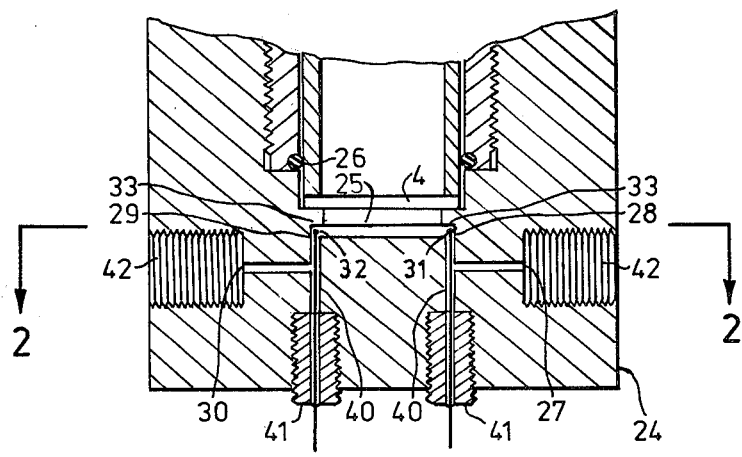
FIG. 1A is a view similar to FIG. 1 of an ionization chamber and detection electrode shown in FIG. 1 and drawn to a larger scale.
Figure 2:
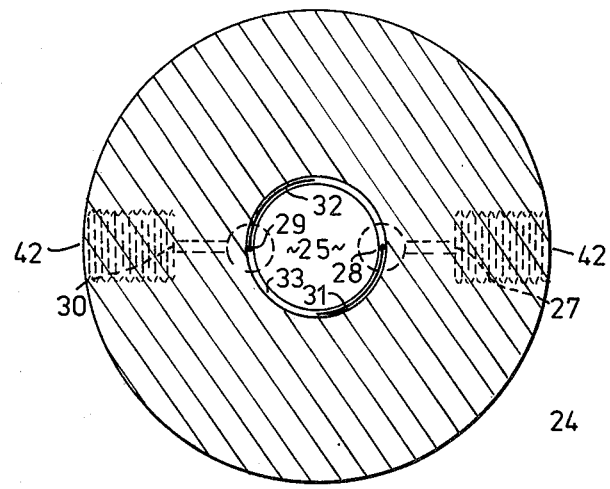
FIG. 2 is a sectional top view on line 2—2 in FIG. 1A.
Figure 3:
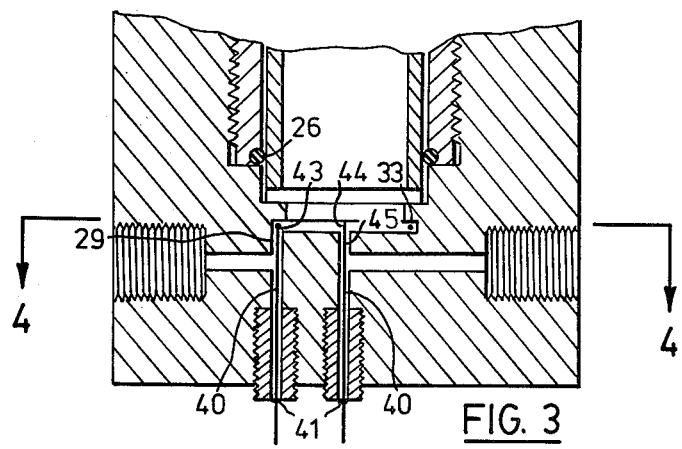
FIG. 3 is a view similar to FIG. 1A of an alternative embodiment of electrode configuration.
Figure 4:
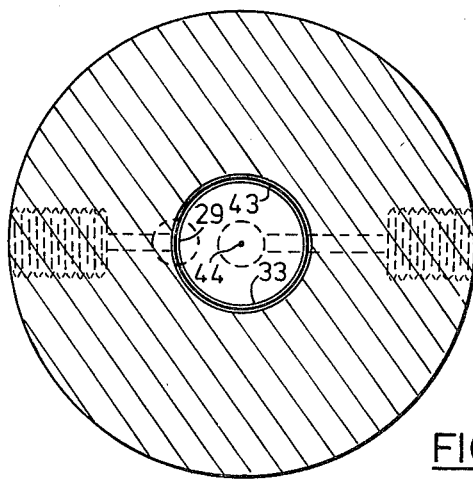
FIG. 4 is a top view on line 4—4 of FIG. 3.

As seen in FIG. 2, the electrodes are two symmetrically opposed curved wires placed circumferentially in the ionization chamber recess 33. They are connected as shown in FIG. 1A by leads within the body 24 and away from the immediate vicinity of the ionization chamber. The electrode leads are routed through respective channels 40 separated from the carrier gas passages 27, 28, and 29, 30 and exit from the body via two gas-tight threaded plugs 41. The gas entrance and exit channels 27 and 30 terminate at two gas-fittings (not shown) which screw into respective threaded recesses 42.

A metal casing or cover 50 is positioned around the body 24 and secured with screws (not shown) to the metal bulkhead 20 in such a manner as to complete the screening of the photoionization detector from external stray fields. Apart from enclosing the body 24, cover 50 may be made sufficiently large to enclose associated parts which are not shown. These include an ambient temperature gas chromatograph column and a chromatographic injection port or sample-loop system. A high voltage power supply (or dry batteries) 52 of approximately 200 volts DC is also included. The cathode electrode lead 53 passes through the housing 50 using a low leakage radio frequency interference filter 55 and hence passes to an electrometer (not shown).

Figure 7:
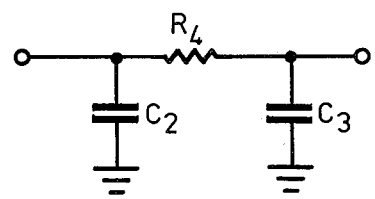
FIG. 7 is a schematic of a filter circuit used in the detector.

The filter 55, whose circuit is illustrated in FIG. 7, has the following typical components:

| | |
|---|---|
| $C_2$ | 10 pf |
| $C_3$ | 10 pf |
| $R_4$ | 10 M |

Figure 6:
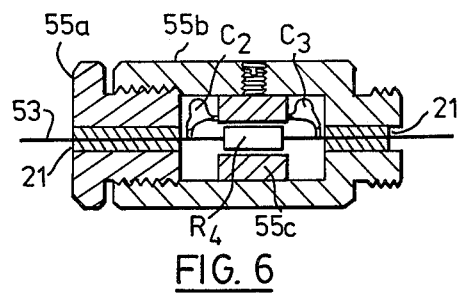
FIG. 6 is a sectional view of a low leakage radio frequency interference filter used to connect an electrometer to the detector.

The physical structure of the filter is illustrated in FIG. 6, in which a three piece metal casing 55a, 55b and 55c houses the components. Lead 53 passes out through insulating bushings 21.

Although not illustrated, provision is made for carrier gas inlet and outlet connections and access for an injection port or a sample-loop system. The positive terminal of the power supply or batteries 52 is connected to the anode electrode lead 56 while the negative terminal 57 is connected to ground.

Leads 17 and 18 from the circuit board 10 penetrate the cover 50 via radio frequency interference filters 61 to supply power to the oscillator circuit shown in FIG. 5.

It will be evident that some variations may be made to the preferred structure described without departing from the invention. For instance the window 4 may be of any material capable of being attached to the main body 2 and permitting transmission of vacuum ultraviolet light. Such materials include lithium fluoride, barium fluoride, strontium fluoride, calcium fluoride and sapphire. The holder 3 may also be of an equivalent dielectric to polytetrafluoroethylene and the window can be attached using a high temperature polymer adhesive.

The gas discharge tube may also be varied by substituting different gases as well as by varying the size of the tube. Other suitable gases include xenon and argon. Also the strip 9 used to enhance the shape of the electromagnetic field and to speed up the firing of the tube, may be varied and may have to be adjusted for different applications. However it has been found that when used with discharge tubes of the size described, it should have an axial extent in the range ½ to 1 inch.

The sensitivity of the detector is enhanced because there is no dead space in the ionization chamber, that is substantially the entire cross sectional area of the chamber is irradiated by ionizing radiation. The radiation level will be substantially uniform in any plane transverse to the axial direction of travel of radiation entering the chamber and if an inert carrier gas such as helium is used, the ultraviolet light released by the radiation source can be substantially uniform throughout the whole ionization chamber because this gas is transparent to the radiation.

The arrangement of electrodes 31 and 32 is important. Any variations to the preferred embodiment should be made only if the lines of force of the electrostatic field created between the two electrodes are maintained in a plane substantially perpendicular to the line of travel of the light radiation entering the ionization chamber from the radiation source. Variations from this will reduce the effectiveness of the device.

Because inductively coupled radio frequency excitation is used, care must be taken to eliminate stray electromagnetic waves from interfering with the electrometer circuitry. The metal casing around the inductor and the detector is advisable as well as the appropriate use of radio frequency interference filters to prevent the release of radio frequency waves from the inductor, which waves might interfere with the operation of the electrometer.

By use of inductively-coupled RF excitation it is possible to deliver a high level of light intensity. The krypton tube described above delivers simultaneously approximately $10^{15}$ photons per second at the 1235 A.U. wavelength and approximately $10^{14}$ photons per second at the 1165 A.U. wavelength. The result of this high intensity is that a larger percentage of the chemical species are ionized and remain ionized and are captured by the detector electrodes. Further the presence of such radiation greatly increases the range of compounds which can be detected by this invention.

The pressure of the inert gas in the discharge tube can vary between 0.1 Torr and 5 Torr and achieve workable results. For most photoionization applications, a pressure of about 3 to 3.5 Torr is preferable.

One alternate arrangement of the electrodes is shown in 3 and 4. In this arrangement the cathode electrode 43 takes the form of an annulus encircling the entire ionization chamber and recessed into slot 33 to be out of the axial flow from the discharge tube. This electrode is housed in the carrier gas exit passage 29 and in the earlier arrangement. Anode 44 is contained in the ionization chamber through the gas entrance 45 which in this arrangement is located along the cylindrical axis of the ionization chamber 25 and extends approximately 1 millimeter into the chamber 25. The electrode leads 40 exit via gas tight fittings 41 as in the earlier arrangement.

This invention should not be limited in scope by the embodiments shown which are representative of structures and methods defined fully in the accompanying claims.

What I claim as my invention is:

1. A device for projecting ultraviolet radiation into a chamber containing electrodes used to sense ionization of chemical species passing through the chamber in the ultraviolet radiation, the device comprising:

a sealed non-metallic tube containing an inert gas at a reduced pressure, the tube having a window at an end of the tube lying transversely of the axis of the tube, the window being transparent to ultraviolet light and being adapted to form a wall of said chamber;

dielectric means positioned about the tube; and an electrically conductive coil supported by the dielectric means and extending concentrically about the tube, the coil being adapted to be connected to a radio frequency source tuned to excite the inert gas inductively sufficient to cause ultraviolet radiation axially through the window for use in the chamber to ionize the chemical species.

2. A device as claimed in claim 1 in which the inert gas is one of the gases in the group: krypton, xenon and argon.

3. A device as claimed in claim 1 in which the window is made from one of the materials in the group: magnesium fluoride, lithium fluoride, barium fluoride, strontium fluoride, calcium fluoride and sapphire.

4. A detector for use in sensing ionizable chemical species in a carrier gas, the detector comprising:

a source of ultraviolet radiation including a non-metallic tube containing an inert gas at reduced pressure; a window at the end of the tube, the window being of a material transparent to ultraviolet light; and coil means coupled about the tube and adapted to be connected to a radio frequency source tuned to excite the inert gas inductively sufficient to cause ultraviolet radiation axially through the window;

dielectric means combining with an outer surface of the window to define a chamber having a transverse cross-section corresponding essentially to that of the inside of the tube and in alignment with the tube;

recess means bordering the chamber;

a cathode contained in the recess means so that the cathode is out of direct alignment with radiation emerging from the window and into the chamber;

an anode spaced from the cathode in at least one of the chamber and recess means; and means defining an inlet to and an outlet from the chamber to direct a flow of gas carrying said species through the chamber whereby ionization can be detected using the anode and the cathode in a suitable electrical sensing circuit.

5. A detector for use in identifying ionizable species carried in a stream of purified air; the detector comprising:

a cylindrical glass tube disposed about a longitudinal axis and having a sealed first end and a window at the other end, the window being of a material transparent to ultraviolet radiation, and the tube containing an inert gas at reduced pressure;

a dielectric sleeve about the tube and in close proximity with the tube;

an electrically conductive coil supported by the sleeve;

a source of radio frequency coupled to the coil for electromagnetic energizing of the gas, the radio frequency being tuned so that the gas is energized to provide ultraviolet radiation which progresses axially of the tube and passes through the window;

dielectric means combining with the window to define a shallow cylindrical chamber disposed about said axis and corresponding in diameter to the inside diameter of the tube, and a recess positioned radially outwards of the chamber;

a cathode located in the recess so that the cathode is out of alignment with radiation coming directly from the tube;

an anode contained in the dielectric means and spaced from the cathode; and sensor means coupled to the anode and to the cathode and responsive to signals caused by the presence of the ionized species in the chamber between the anode and the cathode.

* * * * *